(12) United States Patent
Simpkins et al.

(10) Patent No.: US 7,589,783 B2
(45) Date of Patent: Sep. 15, 2009

(54) CAMERA AND ILLUMINATION MATCHING FOR INSPECTION SYSTEM

(75) Inventors: Patrick Simpkins, Edina, MN (US); Cory Watkins, Chanhassen, MN (US)

(73) Assignee: Rudolph Technologies, Inc., Flanders, NJ (US)

( * ) Notice: Subject to any disclaimer, the term of this patent is extended or adjusted under 35 U.S.C. 154(b) by 906 days.

(21) Appl. No.: 10/890,862

(22) Filed: Jul. 14, 2004

(65) Prior Publication Data

US 2005/0052530 A1 Mar. 10, 2005

Related U.S. Application Data

(60) Provisional application No. 60/486,949, filed on Jul. 14, 2003.

(51) Int. Cl.
- H04N 7/18 (2006.01)
- H04N 5/222 (2006.01)
- H04N 5/20 (2006.01)

(52) U.S. Cl. .................. 348/370; 348/131; 348/255

(58) Field of Classification Search .................. 348/86, 348/87, 91–93, 125, 126, 129, 130, 132, 348/370, 371, 131, 255
See application file for complete search history.

(56) References Cited

U.S. PATENT DOCUMENTS

| | | | |
|---|---|---|---|
| 4,328,553 A | 5/1982 | Fredriksen et al. | |
| 4,464,705 A | 8/1984 | Horowitz | |
| 4,644,172 A | 2/1987 | Sandland et al. | |
| 4,823,394 A | 4/1989 | Berkin et al. | |
| 5,091,963 A | 2/1992 | Litt et al. | |
| 5,497,381 A | 3/1996 | O'Donoghue et al. | |
| 5,592,295 A | 1/1997 | Stanton et al. | |
| 5,640,200 A | 6/1997 | Michael | |
| 5,641,960 A | 6/1997 | Okubo et al. | |
| 5,787,190 A | 7/1998 | Peng et al. | |
| 5,822,055 A | 10/1998 | Tsai et al. | |
| 5,850,466 A | 12/1998 | Schott | |
| 5,856,844 A | 1/1999 | Battermann et al. | |
| 5,917,588 A | 6/1999 | Addiego | |
| 5,949,901 A | 9/1999 | Nichani et al. | |
| 6,137,303 A | 10/2000 | Deckert et al. | |
| 6,140,254 A | 10/2000 | Endisch et al. | |
| 6,147,357 A | 11/2000 | Nicolescu | |
| 6,153,361 A | 11/2000 | Liu et al. | |
| 6,239,554 B1* | 5/2001 | Tessadro et al. | 315/149 |

(Continued)

OTHER PUBLICATIONS

RS-10A/B & RS-3 NIST-Traceable Calibration Light Source, retrieved from archive.org, http://web.archive.org/web/20010421145019/www.gamma-sci.com/rs-10a-b-rs-3-source.htm, Mar. 2, 2000.*

*Primary Examiner*—Timothy J Henn
(74) *Attorney, Agent, or Firm*—Dicke, Billig & Czaja, PLLC (57) ABSTRACT

An inspection tool includes a camera having a gain value and an offset value set to provide a first camera output indicating a first desired average gray value when the camera is illuminated with a precision light source set at a first light level. The inspection tool includes an inspection light source configured to be set at a second light level such that when the inspection light source illuminates a known target, the camera provides a second output indicating a second desired average gray value.

13 Claims, 5 Drawing Sheets

U.S. PATENT DOCUMENTS

| | | |
|---|---|---|
| 6,314,379 B1 | 11/2001 | Hu et al. |
| 6,324,298 B1 | 11/2001 | O'Dell et al. |
| 6,412,326 B1 | 7/2002 | Hubbard et al. |
| 6,542,180 B1* | 4/2003 | Wasserman et al. ......... 348/131 |
| 6,565,920 B1 | 5/2003 | Endisch |
| 6,640,151 B1 | 10/2003 | Somekh et al. |
| 6,708,074 B1 | 3/2004 | Chi et al. |
| 6,724,423 B1* | 4/2004 | Sudo ......................... 348/188 |
| 6,987,534 B1* | 1/2006 | Seta ........................ 348/229.1 |
| 2003/0030050 A1 | 2/2003 | Choi |
| 2003/0202178 A1 | 10/2003 | Tsuji et al. |
| 2004/0201669 A1* | 10/2004 | Guha et al. ................. 348/126 |
| 2005/0041850 A1* | 2/2005 | Watkins et al. .............. 382/145 |

* cited by examiner

CAMERA AND ILLUMINATION MATCHING FOR INSPECTION SYSTEM

CROSS-REFERENCE TO RELATED APPLICATIONS

This application claims the benefit of U.S. Provisional Application Ser. No. 60/486,949, filed Jul. 14, 2003.

BACKGROUND

1. Technical Field

The present invention relates to camera and illumination matching for an inspection system.

2. Background Information

Over the past several decades, the semiconductor has exponentially grown in use and popularity. The semiconductor has in effect revolutionized society by introducing computers, electronic advances, and generally revolutionizing many previously difficult, expensive and/or time consuming mechanical processes into simplistic and quick electronic processes. This boom in semiconductors has been fueled by an insatiable desire by business and individuals for computers and electronics, and more particularly, faster, more advanced computers and electronics whether it be on an assembly line, on test equipment in a lab, on the personal computer at one's desk, or in the home electronics and toys.

The manufacturers of semiconductors have made vast improvements in end product quality, speed and performance as well as in manufacturing process quality, speed and performance. However, there continues to be demand for faster, more reliable and higher performing semiconductors.

Product developers who are building semiconductors and like microelectronics must be able to provide ample illumination for the machine vision process. One type of illumination involves strobing, and it is critical during strobing of the illuminator that the camera shutter is timed correctly—and often this timing alone is not accurate enough to match intensities. Users of inspection equipment continue to demand better defect data thereby requiring better camera and illumination matching.

It is known that cameras that are installed on inspection equipment are pre-set with vendor default settings for camera gain and offset. However, this often results in large variations between systems. In addition, light sources, whether halogen or strobe, can have large variations in light output (photons) for a given applied voltage.

As a result, inspection system users desire that all inspection systems give the same signal output for a given signal input. The output signal is measured as the average CCD array or other sensor array value and the input signal is generated from light reflected off a target or item to be inspected.

Overall, for a given signal input, which is determined from the voltage applied to the light source, a large variation in signal output can occur from the physics of the light source and camera gain and offset settings.

SUMMARY

One embodiment of the present invention provides an inspection tool. The inspection tool includes a camera having a gain value and an offset value set to provide a first camera output indicating a first desired average gray value when the camera is illuminated with a precision light source set at a first light level. The inspection tool includes an inspection light source configured to be set at a second light level such that when the inspection light source illuminates a known target, the camera provides a second output indicating a second desired average gray value.

BRIEF DESCRIPTION OF THE DRAWINGS

Preferred embodiments of the invention, illustrative of the best mode in which Applicant has contemplated applying the principles, are set forth in the following description and are shown in the drawings and are particularly and distinctly pointed out and set forth in the appended claims.

Similar numerals refer to similar parts throughout the drawings.

DETAILED DESCRIPTION

Figure 1:
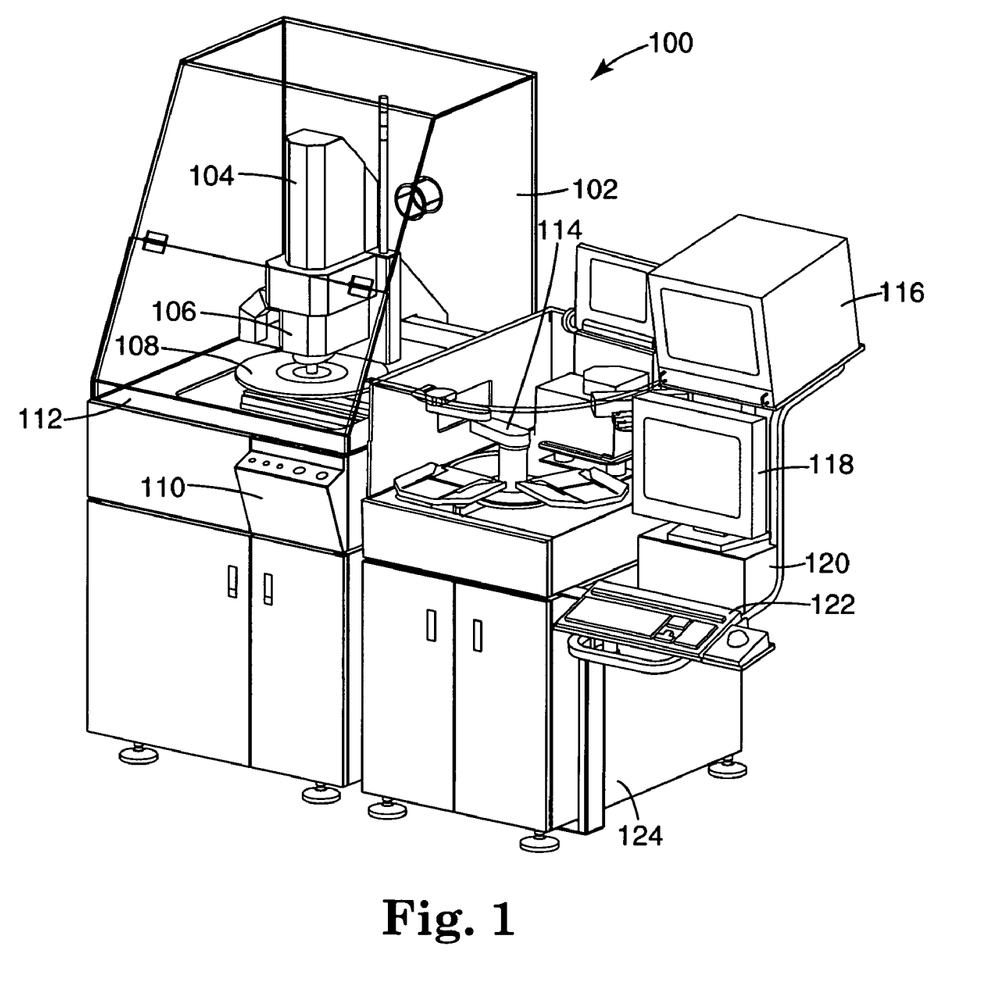
FIG. 1 is a diagram illustrating one embodiment of a semiconductor inspection system.

FIG. 1 is a diagram illustrating one embodiment of a semiconductor inspection system 100. Semiconductor inspection system 100 includes a hood 102, a camera 104, an inspection light source 106, a wafer test plate 108, a wafer alignment device 112, a control panel 110, a robot 114, a display 116, a system parameters display 118, a computer system or controller 120, a parameter input device 122, and a frame 124. In one embodiment, semiconductor inspection system 100 is an automated system that is configured to inspect substrates, such as semiconductor wafers and semiconductor die.

Camera 104 is used for visual inputting of good die during training and for visual inspection of other unknown quality die during inspection. The camera may be any type of camera capable of high resolution inspection. An example of such a camera is a charge-coupled device (CCD) inspection camera used to capture die or other images during defect analysis. In one embodiment, camera 104 is a high resolution CCD camera that provides high resolution gray scale images for inspection.

Robot 114 provides a wafer to test plate 108 for inspection. Wafer alignment device 112 aligns each and every wafer at the same x, y, and θ location or x, y, z, and θ location. Camera 104 is focused on wafer test plate 108 for inspecting wafers.

Computer controlled illumination, including inspection light source 106, is integrated into and with inspection camera 104 and optics to complete the wafer imaging process. Alternatively, the illumination system may be coupled to camera 104 and optics so long as the illumination system works in conjunction with camera 104. In a strobing environment, the illumination must occur simultaneously or substantially simultaneously with camera 104 shuttering, which is in one example a high speed electronic shuttering mechanism. Alternatively, in a non-strobing environment, the illumination is typically continuous or as needed. Illumination may be by any known illumination means such as high intensity lights, lasers, fluorescent lights, arc discharge lamps, incandescent lamps, etc.

Parameter input device 122 is for inputting parameters and other constraints or information. These parameters, constraints, and information include sensitivity parameters, geometry, die sizes, die shape, die pitch, number of rows, number of columns, etc. It is contemplated that any form of input device will suffice, including a keyboard, mouse, scanner, infrared or radio frequency transmitter and receiver, etc.

Display 116 is for displaying the view being seen by camera 104 presently or at any previously saved period. The display is preferably a color monitor or other device for displaying a color display format of the image being viewed by camera 104 for the user's viewing, or alternatively viewing an image saved in memory. In addition, the system parameters display 118 is also available for displaying other information as desired by the user, such as system parameters.

Computer system or controller 120 or other computer device having processing and memory capabilities is for saving the inputted good die, developing a model therefrom, and comparing or analyzing other die in comparison to the model based upon defect filtering and sensitivity parameters to determine if defects exist. Computer system 120 also saves individual pixel gain and offset values from the camera matching process and light source voltage settings from the illumination matching process, which are described below. In addition, computer system 120 is used to perform all other mathematical and statistical functions as well as all operations. In one embodiment, computer system 120 is of a parallel processing DSP environment.

Semiconductor inspection system 100 is camera and illumination matched, such that semiconductor inspection systems that are camera and illumination matched to semiconductor inspection system 100 provide substantially the same camera output in response to substantially the same camera input and inspection light source setting.

In one embodiment, the camera and illumination matching of the present invention comprises matching the response of camera 104 using a precision light source, which is National Institute of Standards and Technology (NIST) traceable, impinging on the charge-coupled device (CCD) array or other sensor array of camera 104. In one embodiment, a software program sends commands to the precision light source to set the desired light level and then the camera CCD average gray value is computed. The test can run for any number of discrete light values, such as 255 values. The two sets of data consisting of target light levels measured in Joules/cm^2 and the average CCD array gray values are fit to an equation of a line, as given by the following Equation I:

$$y_1 = m_1 * x_1 + b_1 \quad \text{Equation I}$$

Where:
$y_1$ = an average gray value;
$x_1$ = a target light level;
$m_1$ = the slope of the line; and
$b_1$ = the intercept of the line.

The values of slope $m_1$ and intercept $b_1$ are compared to target values for slope $m_1$ and intercept $b_1$. If the values are within a desired range, camera 104 passes the test. If the values are outside the desired range, the operator adjusts camera 104 and the test is run again until the gain and offset values of camera 104 are set in the desired range. Once the gain and offset values of camera 104 are set in the desired range, the individual pixel gain and offset values of camera 104 are determined using a similar process.

For illumination matching, a target is placed in semiconductor inspection system 100 on wafer test plate 108. The target is manufactured from a material of known reflectance. The voltage across light source 106 is adjusted until the CCD array average gray value of camera 104 is within a desired range.

Figure 2:
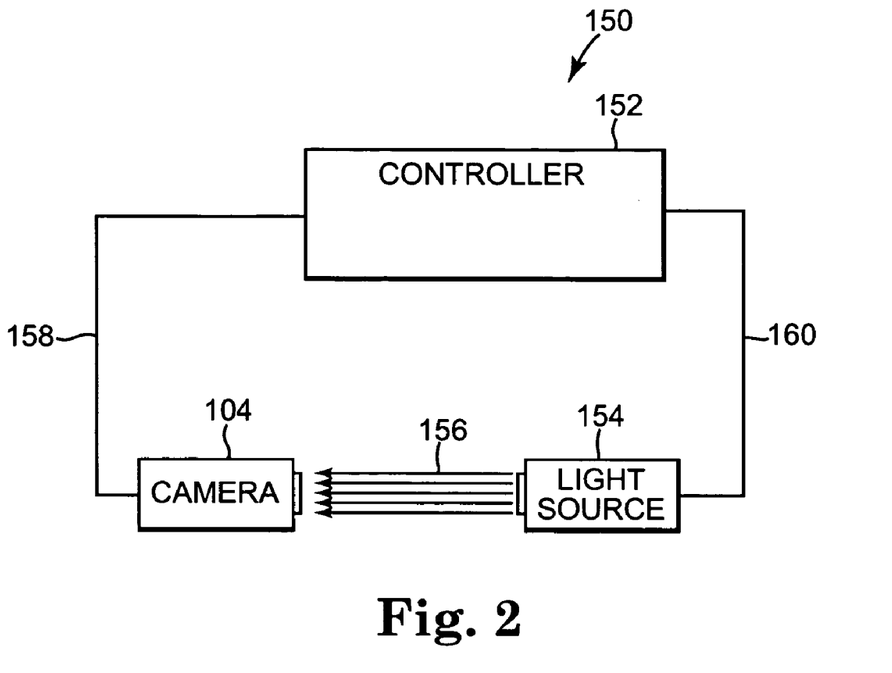
FIG. 2 is a schematic diagram illustrating one embodiment of a camera matching system for camera matching a semiconductor inspection system.

FIG. 2 is a schematic diagram illustrating one embodiment of a camera matching system 150 for camera matching semiconductor inspection system 100. Camera matching of semiconductor inspection system 100 can be performed with camera 104 installed in semiconductor inspection system 100 or by removing camera 104 from semiconductor inspection system 100. Camera matching system 150 includes a controller 152, a precision light source 154, and camera 104. In one embodiment, if camera 104 is installed in semiconductor inspection system 100, controller 152 is included in computer system or controller 120.

Controller 152 is electrically coupled to camera 104 through communication link 158 and to precision light source 154 through communication link 160. Controller 152 controls precision light source 154 through communication link 160 to vary the intensity of light 156 emitted from precision light source 154. In one embodiment, controller 152 controls precision light source 154 to vary the intensity of light 156 emitted from precision light source 154 to 255 distinct light intensities or levels. Controller 152 controls camera 104 and receives image data from camera 104 through communication link 158, including the individual pixel gray values in response to light 156 impinging on the CCD array or other sensor array of camera 104. The gain and offset values of camera 104 are adjusted based on the slope and intercept of an equation of a line fit to the values of the intensity of light 156 emitted from precision light source 154 and the average gray values at each light intensity.

In one embodiment, controller 152 electronically adjusts the gain and offset values of camera 104 through communication link 158. In other embodiments, the gain and offset values of camera 104 are adjusted manually by an operator adjusting potentiometers on camera 104. The method for adjusting the gain and offset values of camera 104, according to one embodiment, is discussed below in more detail with reference to FIG. 4. The same camera matching system 150 is used to determine the individual pixel gain and offset values used for compensating for individual pixel variation in camera 104 during inspection of wafers. The method for determining the individual pixel gain and offset values, according to one embodiment, is discussed below in more detail with reference to FIG. 5.

Figure 3:
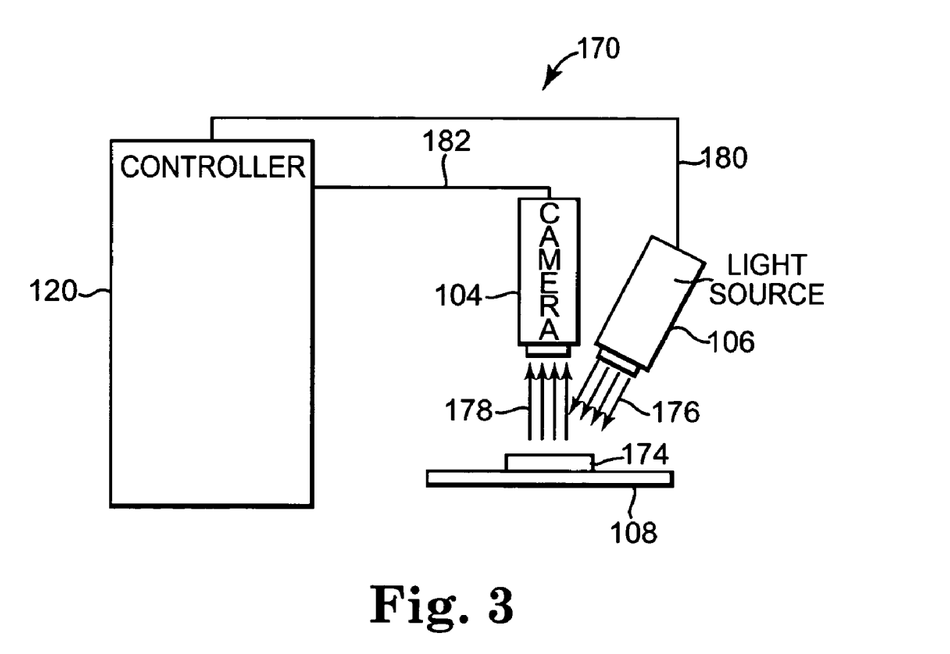
FIG. 3 is a diagram illustrating one embodiment of an illumination matching system for illumination matching a semiconductor inspection system.

FIG. 3 is a diagram illustrating one embodiment of an illumination matching system 170 for illumination matching semiconductor inspection system 100. Illumination matching of semiconductor inspection system 100 is performed on semiconductor inspection system 100. Illumination matching system 170 includes computer system or controller 120, camera 104, inspection light source 106, target 174, and wafer test plate 108. Controller 120 is electrically coupled to inspection light source 106 through communication link 180 and to camera 104 through communication link 182. Target 174 is positioned on wafer test plate 108 underneath camera 104 and illuminated by inspection light source 106. Target 174 is a sample of known reflectance. Controller 120 controls the intensity of light 176 from inspection light source 106 through communication link 180 by controlling a voltage applied to inspection light source 106.

Light 178 reflected from target 174 impinges on the CCD array or other sensor array of camera 104. Controller 120 receives the image data from camera 104 through communication link 182, including the gray values of the individual pixels of the CCD array of camera 104. Controller 120 computes the average gray value for the CCD array of camera 104 from the gray values of the individual pixels of the CCD array of camera 104. Controller 120 adjusts the voltage supplied to inspection light source 106, such that the intensity of light 178 reflected from target 174, as indicated by the average gray value of the CCD array of camera 104, is within a desired range. The method for adjusting light source 106 to illumination match semiconductor inspection system 100, according to one embodiment, is discussed below in more detail in reference to FIG. 6.

Figure 4:
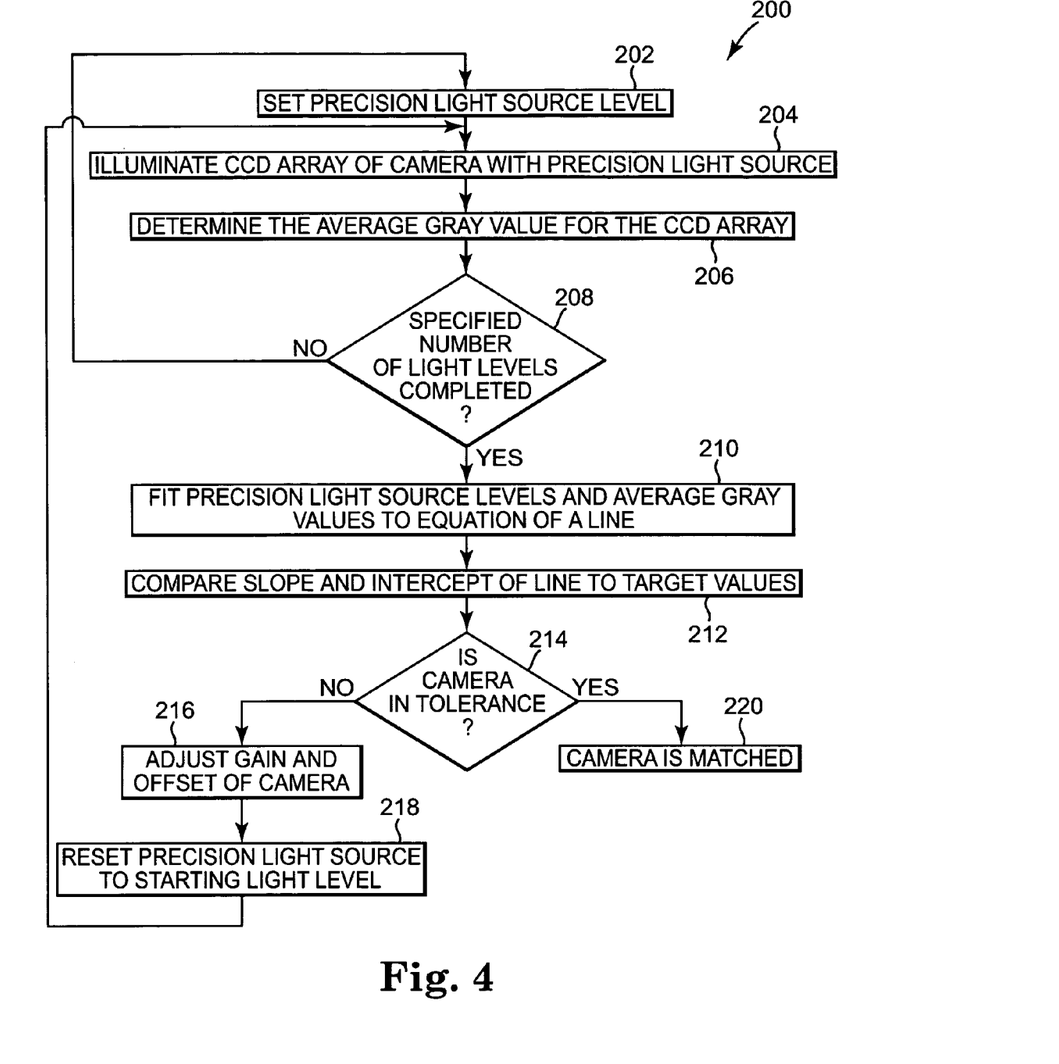
FIG. 4 is a flow diagram illustrating one embodiment of a method for camera matching a camera in a semiconductor inspection system.

FIG. 4 is a flow diagram illustrating one embodiment of a method 200 for camera matching semiconductor inspection system 100. At 202, and with further reference to FIG. 2, precision light source 154 is set to an initial light level out of a plurality of light levels. At 204, precision light source 154 illuminates the CCD array of camera 104 with light 156. At 206, controller 152 determines the average gray value for the CCD array of camera 104. At 208, controller 152 determines whether the average gray value for the CCD array of camera 104 has been determined at each light level of the plurality of light levels. In one embodiment, controller 152 steps precision light source 154 through 255 light levels and determines the average gray value for the CCD array of camera 104 at each of the 255 light levels.

If the average gray value of the CCD array of camera 104 has not been determined at each light level of the plurality of light levels, then the process returns to block 202 where controller 152 adjusts the light level of precision light source 154 to the next light level of the plurality of light levels, and the process repeats. If the average gray value of the CCD array of camera 104 has been determined at each light level of the plurality of light levels, then at 210 the light level values and the average gray values at each light level are fit to an equation of a line, as given by the following Equation II:

$$y_2 = m_2 * x_2 + b_2 \qquad \text{Equation II}$$

Where:
$y_2$=an average gray value;
$x_2$=a light level of precision light source 154;
$m_2$=the slope of the line; and
$b_2$=the intercept of the line.

At 212, controller 152 compares the slope $m_2$ and intercept $b_2$ of the line to desired values. At 214, controller 152 determines whether the slope and intercept are within a desired tolerance. If the slope and intercept are within the desired tolerance, then at 220 camera 104 is matched. If the slope and intercept are not within the desired tolerance, then at 216 the gain and offset of camera 104 are adjusted based on the slope and intercept. At 218, precision light source 154 is reset to the initial light level of the plurality of light levels and the process is repeated until camera 104 is matched.

Figure 5:
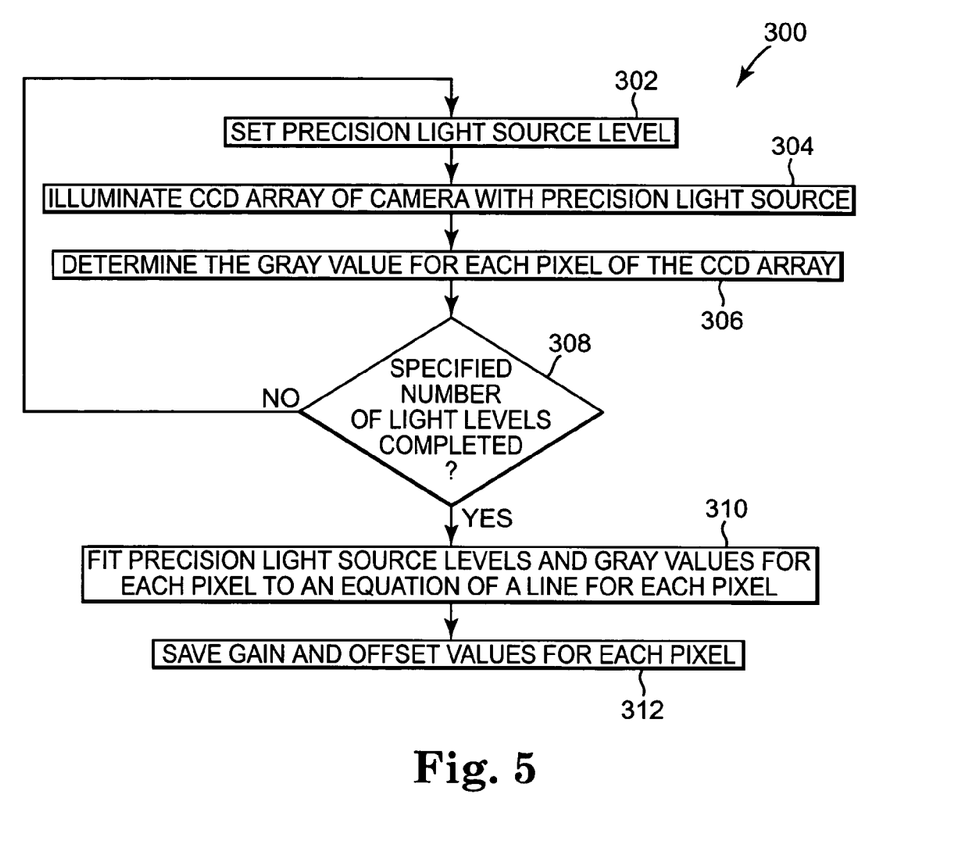
FIG. 5 is a flow diagram illustrating one embodiment of a method for determining the gain and offset values for each pixel of the CCD array of a camera in a semiconductor inspection system.

FIG. 5 is a flow diagram illustrating one embodiment of a method 300 for determining the gain and offset values for each pixel of the CCD array of camera 104. At 302, and with further reference to FIG. 2, precision light source 154 is set to an initial light level of a plurality of light levels. At 304, the CCD array of camera 104 is illuminated with precision light source 154. At 306, controller 152 determines the gray value for each pixel of the CCD array of camera 104. At 308, controller 152 determines whether the gray value for each pixel of the CCD array of camera 104 has been determined at each light level of the plurality of light levels. In one embodiment, controller 152 steps precision light source 154 through 255 light levels and determines the gray value for each pixel of the CCD array of camera 104 at each of the 255 light levels.

If the gray value for each pixel has not been determined at each light level of the plurality of light levels, the process returns to block 302 where precision light source 154 is adjusted to the next light level of the plurality of light levels. If the gray value for each pixel of the CCD array of camera 104 has been determined at each light level of the plurality of light levels, then at 310 controller 152 fits the light levels of precision light source 154 and the gray values for each pixel at each of the light levels to an equation of a line for each pixel, as given by the following equation III:

$$y_3 = m_3 * x_3 + b_3 \qquad \text{Equation III}$$

Where:
$y_3$=a gray value of a pixel;
$x_3$=a light level of precision light source 154;
$m_3$=the slope of the line; and
$b_3$=the intercept of the line.

At 312, the gain and offset values for each pixel determined from the slope $m_3$ and intercept $b_3$ of the equation of the line for each pixel are saved for compensating for individual pixel variation in the CCD array of camera 104 during inspection of wafers.

Figure 6:
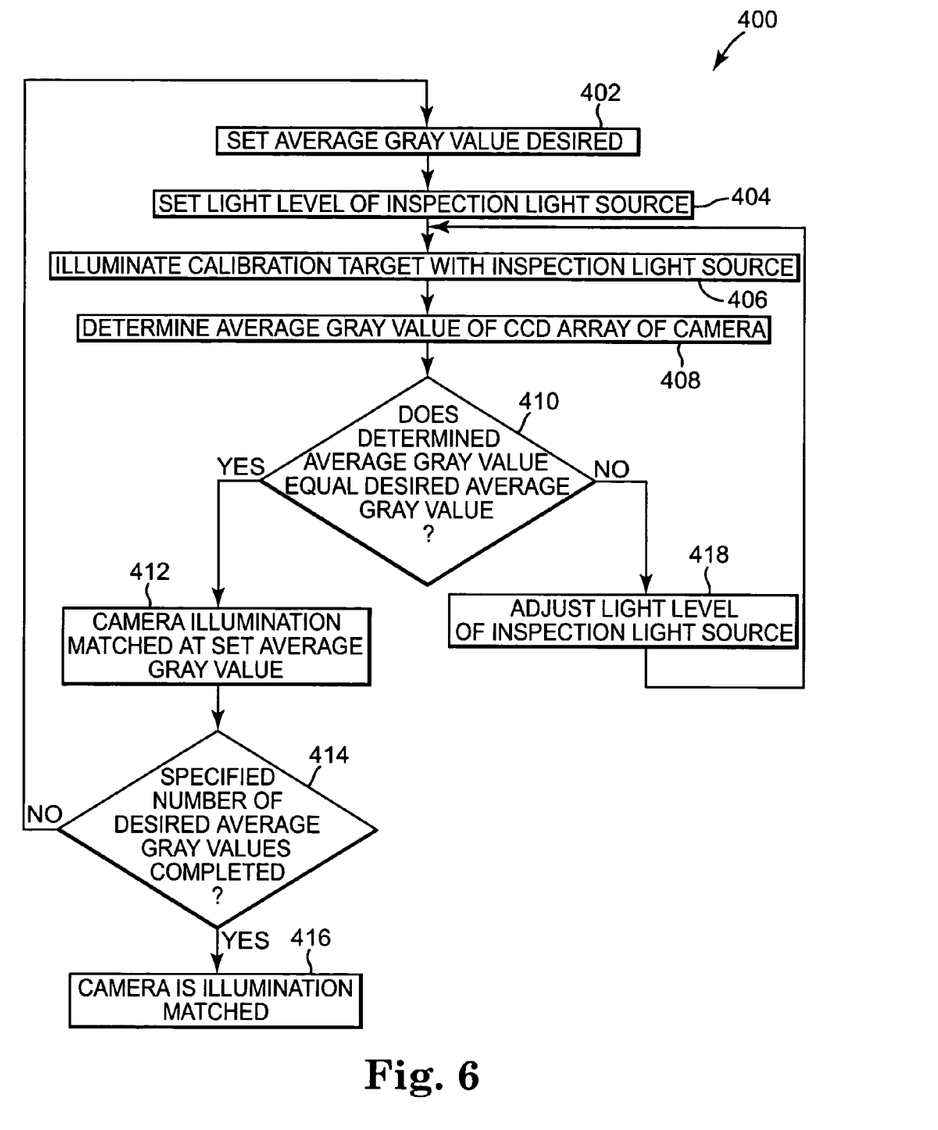
FIG. 6 is a flow diagram illustrating one embodiment of a method for illumination matching an inspection light source in a semiconductor inspection system.

FIG. 6 is a flow diagram illustrating one embodiment of a method 400 for illumination matching semiconductor inspection system 100. At 402, and with further reference to FIG. 3, controller 120 selects a desired average gray value for the CCD array of camera 104. At 404, controller 120 sets the inspection light source 106 setting of inspection light source 106 corresponding to the desired average gray value for the CCD array of camera 104. At 406, inspection light source 106 illuminates target 174 with light 176. At 408, controller 120 determines the average gray value of the CCD array of camera 104 when illuminated with light 178 reflected from target 174. At 410, controller 120 determines whether the determined average gray value is substantially equal to the desired average gray value.

If the determined average gray value is not substantially equal to the desired average gray value, then at 418 the voltage to inspection light source 106 at the current inspection light source 106 setting is adjusted and control returns to block 406 where the process repeats. If the determined average gray value substantially equals the desired average gray value, then at 412 camera 104 is illumination matched at the current inspection light source 106 setting. At 414, controller 120 determines whether the voltage to inspection light source 106 has been set at each inspection light source 106 setting to obtain the desired average gray value at each of the plurality of inspection light source 106 settings. If the voltage has not been set at each inspection light source 106 setting of the plurality of inspection light source 106 settings, then the process returns to block 402 where controller 120 selects the next desired average gray value for the plurality of inspection light source 106 settings, and the process is repeated. If the light source voltage has been set at each inspection light source 106 setting of the plurality of inspection light source 106 settings, then at 416 camera 104 is illumination matched.

In one embodiment, the invention is desirable as it allows for camera and illumination matching for inspection systems where light power settings can be shared between multiple tools. In one embodiment, the invention enables multiple inspection systems to generate a similar image in respect to average light level, contrast, and histograms of the image. In one embodiment, the invention also allows light sources to be replaced in systems and still give the proper output signal for a given input signal.

Accordingly, the invention as described above and understood by one of skill in the art is simplified, provides an effective, safe, inexpensive, and efficient device, system and process which achieves all the enumerated objectives, provides for eliminating difficulties encountered with prior devices, systems and processes, and solves problems and obtains new results in the art.

In the foregoing description, certain terms have been used for brevity, clearness and understanding; but no unnecessary limitations are to be implied therefrom beyond the requirement of the prior art, because such terms are used for descriptive purposes and are intended to be broadly construed.

Moreover, the invention's description and illustration is by way of example, and the invention's scope is not limited to the exact details shown or described.

Having now described the features, discoveries and principles of the invention, the manner in which it is constructed and used, the characteristics of the construction, and the advantageous, new and useful results obtained; the new and useful structures, devices, elements, arrangements, parts and combinations, are set forth in the appended claims.

What is claimed is:

1. An inspection system comprising:
a first inspection tool comprising a first camera, the first camera having a gain value and an offset value set such that the first inspection tool provides an output indicating a first desired average gray value when the first camera is illuminated with a precision light source set at a first light level; and
a second inspection tool comprising a second camera matched to the first camera,
wherein the first inspection tool comprises a first controller, the first controller configured to:
step a light level setting of the precision light source through a plurality of light levels;
illuminate a sensor array of the first camera with the precision light source at each of the plurality of light levels;
determine an average gray value for the sensor array at each of the plurality of light levels;
fit the plurality of light levels and the average gray value at each of the plurality of light levels to a line;
compare a slope and an intercept of the line to desired values; and
adjust the gain and the offset of the first camera based on the comparison.

2. The inspection system of claim 1, wherein the second camera is configured to be matched to the first camera by adjusting the gain and the offset of the first camera and a gain and an offset of the second camera such that an output of the second camera when focused on a target is substantially equal to an output of the first camera when focused on the target.

3. The inspection system of claim 2, wherein the line is in the form y=m*x +b, wherein y is an average gray value, x is a light level, m is the slope of the line, and b is the intercept of the line.

4. The inspection system of claim 3, wherein the second inspection tool comprises a second controller, the second controller configured to adjust the gain and the offset of the second camera in substantially the same manner as the first controller is configured to adjust the first camera.

5. The inspection system of claim 1, wherein the precision light source is National Institute of Standards and Technology (NIST) traceable.

6. The inspection system of claim 1, wherein the first inspection tool comprises a first inspection light source and the second inspection tool comprises a second inspection light source, and wherein the first inspection tool is illumination matched to the second inspection tool.

7. The inspection system of claim 6, wherein the first controller is configured to:
illuminate a target of known reflectance with the first inspection light source;
step the first inspection light source through a plurality of light level settings; and
adjust a first inspection light level at each of the plurality of light level settings until an average gray value of a sensor array of the first camera focused on the target is within a desired range at each of the plurality of light level settings.

8. The inspection system of claim 7, wherein the second controller is configured to:
illuminate the target with the second inspection light source;
step the second inspection light source through the plurality of light level settings; and
adjust a second light level at each of the plurality of light level settings until an average gray value of a sensor array of the second camera focused on the target is within the desired range at each of the plurality of light level settings.

9. An inspection system comprising:
a first inspection tool comprising a first camera, the first camera having a gain value and an offset value set such that the first inspection tool provides an output indicating a first desired average gray value when the first camera is illuminated with a light source providing a first light level; and
a second inspection tool comprising a second camera, the second camera having a gain value and an offset value set such that the second inspection tool provides an output indicating the first desired average gray value when the second camera is illuminated with a light source providing the first light level,
wherein the first inspection tool comprises a first controller, the first controller configured to:
step a light level setting of the light source through a plurality of light levels;
illuminate a sensor array of the first camera with the light source at each of the plurality of light levels;
determine an average gray value for the sensor array at each of the plurality of light level;
fit the plurality of light levels and the average gray value at each of the plurality of light levels to a line;
compare a slope and an intercept of the line to desired values; and
adjust the gain and the offset of the first camera based on the comparison.

10. The inspection system of claim 9, wherein the first camera has a gain value and an offset value for each individual pixel of the first camera such that the first inspection tool provides an output for each pixel of the first camera indicating the first desired gray value when the first camera is illuminated with a light source providing the first light level; and
wherein the second camera has a gain value and an offset value for each individual pixel of the second camera such that the second inspection tool provides an output for each pixel of the second camera indicating the first desired gray value when the second camera is illuminated with a light source providing the first light level.

11. The inspection system of claim 9, wherein the first inspection tool comprises a first inspection light source configured to be set at a second light level such that when the first inspection light source illuminates a known target, the first inspection system provides an output indicating a second desired average gray value; and wherein the second inspection tool comprises a second inspection light source configured to be set at the second light level such that when the second inspection light source illuminates the known target, the second inspection system provides an output indicating the second desired average gray value.

12. An inspection system comprising:

a first inspection tool comprising a first camera and a first inspection light source, the first camera having a gain value and an offset value set such that the first inspection tool provides an output indicating a first desired average gray value when the first camera is illuminated with a precision light source providing a first light level; and a second inspection tool comprising a second camera and a second inspection light source, the second camera having a gain value and an offset value set such that the second inspection tool provides an output indicating the first desired average gray value when the second camera is illuminated with the precision light source providing the first light level, wherein the first inspection light source is illumination matched to the second inspection light source, and wherein the first inspection tool comprises a first controller, the first controller configured to:

step a light level setting of the precision light source through a plurality of light levels;

illuminate a sensor array of the first camera with the precision light source at each of the plurality of light levels;

determine an average gray value for the sensor array at each of the plurality of light levels;

fit the plurality of light levels and the average gray value at each of the plurality of light levels to a line;

compare a slope and an intercept of the line to desired values; and adjust the gain and the offset of the first camera based on the comparison.

13. The inspection system of claim 12, wherein the precision light source is National Institute of Standards and Technology (NIST) traceable.

* * * * *

UNITED STATES PATENT AND TRADEMARK OFFICE
CERTIFICATE OF CORRECTION

PATENT NO. : 7,589,783 B2 Page 1 of 1
APPLICATION NO. : 10/890862
DATED : September 15, 2009
INVENTOR(S) : Patrick Simpkins et al.

It is certified that error appears in the above-identified patent and that said Letters Patent is hereby corrected as shown below:

Column 8, line 43, delete "level" and insert in place thereof --levels--.

Signed and Sealed this

Seventeenth Day of November, 2009

David J. Kappos
*Director of the United States Patent and Trademark Office*

UNITED STATES PATENT AND TRADEMARK OFFICE
CERTIFICATE OF CORRECTION

PATENT NO. : 7,589,783 B2  Page 1 of 1
APPLICATION NO. : 10/890862
DATED : September 15, 2009
INVENTOR(S) : Simpkins et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1249 days.

Signed and Sealed this

Twenty-first Day of September, 2010

David J. Kappos
*Director of the United States Patent and Trademark Office*